United States Patent
Shinagawa et al.

(10) Patent No.: US 11,225,453 B2
(45) Date of Patent: Jan. 18, 2022

(54) METHOD FOR PRODUCING TRICYCLO[5.2.1.02,6]DECANE-2-CARBOXYLATE

(71) Applicant: Mitsubishi Gas Chemical Company, Inc., Chiyoda-ku (JP)

(72) Inventors: Shiori Shinagawa, Kurashiki (JP); Mitsuharu Kitamura, Niigata (JP); Shinichi Nagao, Kurashiki (JP); Ken Sugito, Kurashiki (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 16/970,113

(22) PCT Filed: Feb. 12, 2019

(86) PCT No.: PCT/JP2019/004910
§ 371 (c)(1),
(2) Date: Aug. 14, 2020

(87) PCT Pub. No.: WO2019/159906
PCT Pub. Date: Aug. 22, 2019

(65) Prior Publication Data
US 2021/0107858 A1    Apr. 15, 2021

(30) Foreign Application Priority Data
Feb. 16, 2018   (JP) .............................. JP2018-026132

(51) Int. Cl.
 *C07C 67/36* (2006.01)
 *B01J 27/12* (2006.01)
 *C07C 69/753* (2006.01)

(52) U.S. Cl.
CPC .............. *C07C 67/36* (2013.01); *B01J 27/12* (2013.01); *C07C 69/753* (2013.01); *C07C 2603/10* (2017.05)

(58) Field of Classification Search
CPC ......... C07C 67/14; C07C 67/36; C07C 69/75; C07C 69/753

USPC .......................................................... 560/232
See application file for complete search history.

(56) References Cited

U.S. PATENT DOCUMENTS

| | | | |
|---|---|---|---|
| 4,602,107 A | 7/1986 | Fujikura et al. | |
| 4,973,740 A | 11/1990 | Ishihara et al. | |
| 2005/0101799 A1 | 5/2005 | Kitamura et al. | |

FOREIGN PATENT DOCUMENTS

| JP | 61-1014 | B2 | | 1/1986 |
|---|---|---|---|---|
| JP | 09194433 | | * | 7/1997 |
| JP | 2680069 | B2 | | 11/1997 |
| JP | 2005-89399 | A | | 4/2005 |
| JP | 2005-89400 | A | | 4/2005 |
| JP | 2006-248957 | A | | 9/2006 |
| JP | 6140658 | B2 | | 5/2017 |
| JP | 6253499 | B2 | | 12/2017 |

OTHER PUBLICATIONS

Machine translation of JP-09194433, 1997.*
International Search Report dated Apr. 16, 2019 in PCT/JP2019/004910 filed on Feb. 12, 2019, citing documents AC and AS-AU therein, 1 page.

* cited by examiner

*Primary Examiner* — Ana Z Muresan
(74) *Attorney, Agent, or Firm* — Oblon, McClelland, Maier & Neustadt, L.L.P.

(57) ABSTRACT

A method for producing tricyclo[5.2.1.0$^{2,6}$]decane-2-carboxylate according to the present invention is a method for producing tricyclo[5.2.1.0$^{2,6}$]decane-2-carboxylate, containing reacting tricyclo[5.2.1.0$^{2,6}$]deca-3-ene in a dilute solution containing the tricyclo[5.2.1.0$^{2,6}$]deca-3-ene with carbon monoxide in the presence of an acid catalyst, followed by reaction with an alcohol, wherein the dilute solution contains 100 parts by mass or more of a tricyclo [5.2.1.0$^{2,6}$]decane isomer mixture based on 100 parts by mass of the tricyclo[5.2.1.0$^{2,6}$]deca-3-ene, the tricyclo [5.2.1.0$^{2,6}$]decane isomer mixture contains endo-tricyclo [5.2.1.0$^{2,6}$]decane (Endo form of TCD) and exo-tricyclo [5.2.1.0$^{2,6}$]decane (Exo form of TCD), and a constituent ratio thereof (Endo form of TCD/Exo form of TCD) is greater than 1.0.

7 Claims, No Drawings

METHOD FOR PRODUCING TRICYCLO[5.2.1.02,6]DECANE-2-CARBOXYLATE

TECHNICAL FIELD

The present invention relates to a method for producing tricyclo[5.2.1.0$^{2,6}$]decane-2-carboxylate.

BACKGROUND ART

Conventionally, as a method for producing a carboxylate from a monoolefin, a method has been known that includes reacting an olefin with carbon monoxide and water in a strong acid by the Koch reaction, and then esterifying the obtained carboxylic acid in an acid catalyst.

Tricyclo[5.2.1.0$^{2,6}$]decane-2-carboxylate (hereinafter also referred to as TCDCE) is excellent in fragrance and useful as a perfume or a perfume component. When TCDCE is produced, a method is adopted that includes converting tricyclo[5.2.1.0$^{2,6}$]deca-3-ene (dihydrodicyclopentadiene, hereinafter also referred to as DHDCPD) obtained by hydrogenating dicyclopentadiene (hereinafter also referred to as DCPD) into tricyclo[5.2.1.0$^{2,6}$]decane-2-carboxylic acid (hereinafter also referred to as TCDC) by reaction with carbon monoxide and water in a strong acid such as sulfuric acid, and esterifying TCDC. But, cycloolefins polymerize easily in carbonylation reactions, and TCDC cannot be obtained in high yield.

In view of such circumstances, Patent Document 1 describes a method that includes reacting DCPD and formic acid, followed by hydrogenation to obtain tricyclo[5.2.1.0$^{2,6}$]dec-8-yl formate, and reacting the tricyclo[5.2.1.0$^{2,6}$]dec-8-yl formate and an inorganic strongly acidic catalyst in contact with each other to obtain tricyclo[5.2.1.0$^{2,6}$]decane-2-carboxylic acid.

In order to utilize TCDC as a perfume, it is necessary to perform esterification. Generally, the esterification of a tertiary carboxylic acid is difficult, and particularly in the case of TCDC, the influence of steric hindrance is large. In view of these, Patent Document 2 discloses a method in which an acid halide is derived from TCDC and then esterified with an alcohol. In Patent Documents 2 and 3, a dialkyl sulfate as an esterifying agent is allowed to act on TCDC to perform esterification.

Further, Patent Document 4 discloses a method in which DHDCPD, carbon monoxide, and an alcohol are reacted in hydrogen fluoride (HF) by the reaction shown in the following Scheme 1 to cause a carbonylation reaction and an esterification reaction at the same time to obtain TCDCE in high yield. This method is a method promising in industrial practice because the ester can be obtained in situ without separating the carboxylic acid but with ease of the recovery of HF (catalyst).

Scheme 1

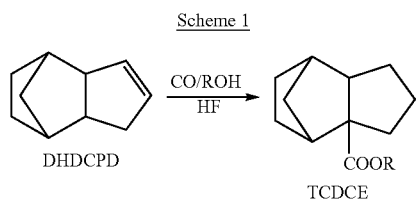

Patent Document 5 describes a production method that includes, in the presence of HF, reacting DHDCPD with carbon monoxide to obtain an acyl fluoride, and then reacting the acyl fluoride with an alcohol to obtain TCDCE.

CITATION LIST

Patent Document

Patent Document 1: Japanese Patent Publication No. 61-40658
Patent Document 2: Japanese Patent Publication No. 61-1014
Patent Document 3: Japanese Patent Publication No. 62-53499
Patent Document 4: Japanese Patent No. 2680069
Patent Document 5: Japanese Patent Laid-Open No. 2005-89399

SUMMARY OF INVENTION

Technical Problem

But, the method described in Patent Document 1 cannot be said to be economical because strong acids such as sulfuric acid and HF are consumed in large amounts.

The method described in Patent Document 2 cannot be said to be economical because an expensive halogenating agent is used in a large amount. Another problem is that the dialkyl sulfate used is expensive and undergoes decomposition by the water produced by the reaction.

A problem of the method described in Patent Document 3 is that the dialkyl sulfate used is expensive and further undergoes decomposition by the water produced by the reaction.

In the method described in Patent Document 4, the conditions of a low reaction temperature of –10° C. or less and a molar ratio of HF to DHDCPD (HF/DHDCPD) of 15 times or more are necessary for obtaining TCDCE. Under these conditions, the reaction yield is low, and HF, the catalyst, is used in a large amount, resulting in significantly low productivity. Thus, the method is a method difficult to industrially carry out.

In the method described in Patent Document 5, TCDCE cannot be obtained in high yield, and there is room for improvement.

The present invention has been made in view of the above problems, and it is an object of the present invention to provide a method for producing TCDCE, which is an excellent perfume, industrially simply, in high yield, and efficiently.

Solution to Problem

The present inventors have found that the cause of the decrease in reaction yield in the method described in Patent Document 4 is a decrease in the acid strength of HF due to the ester produced in the system and the unreacted alcohol. Accordingly, the present inventors have diligently studied a method of separating the steps of carbonylation and esterification to maintain the acid strength of an acid catalyst such as a catalyst comprising hydrogen fluoride (HF) (hereinafter also referred to as a HF catalyst) to improve reaction yield. As a result, the present inventors have found that TCDCE excellent in fragrance and useful as a perfume or a perfume component is obtained industrially simply, in high yield, and efficiently by using a dilute solution comprising tricyclo[5.2.1.0$^{2,6}$]deca-3-ene in a carbonylation reaction, the dilute solution comprising 100 parts by mass or more of a tricyclo[5.2.1.0$^{2,6}$]decane (hereinafter also referred to as TCD) isomer mixture based on 100 parts by mass of the tricyclo[5.2.1.0$^{2,6}$]deca-3-ene, wherein the TCD isomer mixture comprises endo-tricyclo[5.2.1.0$^{2,6}$]decane (Endo form of TCD) and exo-tricyclo[5.2.1.0$^{2,6}$]decane (Exo form of TCD) in a constituent ratio thereof (Endo form of TCD/Exo form of TCD) of greater than 1.0. Thus, the present inventors have completed the present invention.

Specifically, the present invention includes the following aspects.

[1] A method for producing tricyclo[5.2.1.0$^{2,6}$]decane-2-carboxylate, comprising reacting tricyclo[5.2.1.0$^{2,6}$]deca-3-ene in a dilute solution comprising the tricyclo[5.2.1.0$^{2,6}$]deca-3-ene with carbon monoxide in the presence of an acid catalyst, followed by reaction with an alcohol, wherein the dilute solution comprises 100 parts by mass or more of a tricyclo[5.2.1.0$^{2,6}$]decane isomer mixture based on 100 parts by mass of the tricyclo[5.2.1.0$^{2,6}$]deca-3-ene, the tricyclo[5.2.1.0$^{2,6}$]decane isomer mixture comprises endo-tricyclo[5.2.1.0$^{2,6}$]decane (Endo form of TCD) and exo-tricyclo[5.2.1.0$^{2,6}$]decane (Exo form of TCD), and a constituent ratio thereof (Endo form of TCD/Exo form of TCD) is greater than 1.0.

[2] The method for producing tricyclo[5.2.1.0$^{2,6}$]decane-2-carboxylate according to [1], wherein an amount of the acid catalyst used is 4 to 25-fold moles based on the tricyclo[5.2.1.0$^{2,6}$]deca-3-ene.

[3] The method for producing tricyclo[5.2.1.0$^{2,6}$]decane-2-carboxylate according to [1] or [2], wherein in reacting the tricyclo[5.2.1.0$^{2,6}$]deca-3-ene in the dilute solution comprising the tricyclo[5.2.1.0$^{2,6}$]deca-3-ene with the carbon monoxide, a partial pressure of the carbon monoxide is 0.5 to 5 MPaG.

[4] The method for producing tricyclo[5.2.1.0$^{2,6}$]decane-2-carboxylate according to any of [1] to [3], wherein the alcohol comprises ethanol.

[5] The method for producing tricyclo[5.2.1.0$^{2,6}$]decane-2-carboxylate according to any of [1] to [4], wherein the acid catalyst is a catalyst comprising hydrogen fluoride.

Advantageous Effects of Invention

According to the production method of the present invention, TCDCE useful as a perfume raw material can be obtained industrially simply, in high yield, and efficiently, and therefore the production method of the present invention is industrially extremely useful.

DESCRIPTION OF EMBODIMENTS

A mode for carrying out the present invention (hereinafter simply referred to as "this embodiment") will be described below. This embodiment below is an illustration for describing the present invention, and the present invention is not limited to only this embodiment.

The method for producing TCDCE in this embodiment contains the step of carbonylating DHDCPD in a dilute solution containing DHDCPD with carbon monoxide to obtain a carbonyl compound, and then the step of esterifying the carbonyl compound with an alcohol.

[Carbonylation of DHDCPD]

The carbonyl reaction of DHDCPD is carried out in the presence of an acid catalyst under the pressure of carbon monoxide, and DHDCPD in a dilute solution containing DHDCPD is carbonylated with carbon monoxide to obtain a carbonyl compound.

In this embodiment, the dilute solution containing DHDCPD, a raw material, supplied for carbonylation is obtained by diluting DHDCPD with a TCD isomer mixture. The dilute solution may contain an organic solvent as needed. The dilute solution contains 100 parts by mass or more, preferably 100 to 300 parts by mass, and more preferably 150 to 300 parts by mass of the TCD isomer mixture based on 100 parts by mass of DHDCPD. When the amount of the TCD isomer mixture is smaller than this range, the yield improvement effect is small. When the amount of the TCD isomer mixture is larger than this range, the yield improvement effect is small, and there are possibilities that the cost of separating TCD increases, and that at the same time the volumetric efficiency of the apparatus also decreases.

DHDCPD, which is a raw material, is usually prepared by hydrogenating DCPD by an ordinary method but is not particularly limited.

The TCD isomer mixture contains at least endo-tricyclo[5.2.1.0$^{2,6}$]decane (hereinafter also referred to as the Endo form of TCD) and may contain exo-tricyclo[5.2.1.0$^{2,6}$]decane (hereinafter also referred to as the Exo form of TCD). The TCD isomer mixture of this embodiment also includes a case of only the Endo form of TCD. The constituent ratio of the Endo form of TCD to the Exo form of TCD (Endo form of TCD/Exo form of TCD) is usually greater than 1.0, preferably greater than 1.5, and only the Endo form of TCD (Endo form of TCD/Exo form of TCD being 100/0) is more preferred.

By using the TCD isomer mixture in the form of a diluent solvent, the suppression of DHDCPD polymerization in the acid catalyst can be effectively achieved. In addition, TCD is obtained by hydrogenating all two double bonds of DCPD, but also is a compound produced in no small amount during the carbonylation reaction of DHDCPD in the acid catalyst, and therefore TCD is also considered as an equilibrium product in this reaction system. Although only speculation, it is considered that by previously adding TCD into this reaction system, the production of TCD and the like as by-products during the carbonylation reaction can be suppressed, and that the yield of TCDCE, which is the target material, improves.

For the TCD isomer mixture, a TCD isomer mixture may be obtained by fully hydrogenating DCPD and used or a by-product produced in the reaction may be recovered and used, as long as the constituent ratio of the Endo form of TCD to the Exo form of TCD satisfies the above range.

The organic solvent is not particularly limited, and examples thereof include aliphatic hydrocarbon-based solvents such as n-hexane, n-heptane, cyclohexane, and isooctane. One type of these can be used alone, or two or more types of these can be used in combination. The amount of the organic solvent is not particularly limited but is usually 10 to 150 parts by mass based on 100 parts by mass of DHDCPD.

The acid contained in the acid catalyst is not particularly limited, and known acids can be used. Specific examples include acids containing halogens such as hydrochloric acid (HCl), hydrogen fluoride (HF), and bromine fluoride (HBr), inorganic acids such as sulfuric acid, p-toluenesulfonic acid, phosphoric acid, boron trifluoride-phosphoric acid, and boron trifluoride hydrate, organic acids such as methanesulfonic acid, benzenesulfonic acid, and p-toluenesulfonic acid, boron trifluoride-methanol, and mixtures thereof. One of these acid catalysts can be used alone, or two or more of these acid catalysts can be appropriately mixed and used.

Among these, a HF catalyst is more preferred because of high yield of an acyl fluoride, and high yield of TCDCE with efficiency. It is considered that the reason why the yield of particularly the acyl fluoride increases by using the HF catalyst is that in addition to the effect of suppressing the polymerization of DHDCPD, which is a raw material, in HF, the production of TCD as a by-product during the carbonylation reaction can be effectively suppressed.

In this embodiment, a cuprous compound can also be added as a catalyst component. When the reaction temperature is set at a relatively low temperature, the activity of the carbonylation reaction can be increased even under such a condition by adding the cuprous compound, and TCDCE can be obtained due to high selectivity and high yield. Examples of the cuprous compound include $Cu_2O$, $CuOH$, $Cu_2S$, $Cu_2SO_3 \cdot H_2O$, and $Cu_2Cl_2$. One of these cuprous compounds can be used alone, or two or more of these cuprous compounds can be appropriately mixed and used. The amount of the cuprous compound used is not particularly limited but is usually in the range of 0 to 10% by weight based on the total weight of the catalyst.

When the acid catalyst is composed of two or more catalyst components, the acid catalyst is preferably prepared by mixing or dissolving the catalyst components.

The amount of the acid catalyst used is not particularly limited but is preferably 4 to 25-fold moles, more preferably 5 to 15-fold moles based on DHDCPD. When the molar ratio of the acid catalyst is too low, there is a possibility that the carbonylation reaction does not proceed sufficiently while side reactions such as disproportionation and polymerization occur at the same time, causing decrease in yield. Even if the acid catalyst is used in an amount used higher than this range, the effects such as yield improvement are small, and there are possibilities that the cost of separating the acid catalyst increases, and that the volumetric efficiency of the apparatus also decreases.

When a HF catalyst is used, a substantially anhydrous HF catalyst is preferably used.

Inert gases such as nitrogen and methane may be contained in the carbon monoxide.

The partial pressure of carbon monoxide is not particularly limited but is preferably 0.5 to 5 MPaG, more preferably 1 to 3 MPaG. When the partial pressure of carbon monoxide is too low, there is a possibility that the carbonylation reaction does not proceed sufficiently while side reactions such as disproportionation and polymerization occur at the same time, causing decrease in yield. Even if the partial pressure of carbon monoxide is set higher than this range, there are possibilities that no reaction merit is obtained, and that trouble such as the need for a high pressure apparatus is caused.

The temperature of the carbonylation reaction is not particularly limited but is preferably 0 to 90° C., more preferably in the range of 20 to 70° C. When the reaction temperature is lower than this range, there is a possibility that the amount of the polymerization product produced as a by-product increases. Also when the reaction temperature is higher than this range, there is a possibility that the amount of the polymerization product produced as a by-product increases while many TCDCE isomers are also produced as by-products in this case, causing decrease in yield.

The form of the reaction of carbonylation is not particularly limited, and any of known methods such as semicontinuous and continuous methods can be used.

In this embodiment, in order to remove the by-products produced in the carbonylation reaction, the step of removing the by-products may be additionally included after the carbonylation step.

When a HF catalyst is used, an isomerization step can also be additionally included after the carbonylation step if the isomer ratio of the acyl fluoride or the like is lower than the desired isomer ratio. In this case, the isomerization of the acyl fluoride can be performed in the HF catalyst to perform the adjustment of the isomer ratio.

[Esterification with Alcohol]

The TCDCE according to this embodiment is obtained by reaction with an alcohol following the carbonylation. At this time, after the by-products produced in the carbonylation reaction are once separated, esterification with the alcohol may be performed under the acid catalyst again; however, a method is usually adopted in which the synthetic liquid containing the acid catalyst is reacted with the alcohol as it is, thereby producing TCDCE. At this time, it is preferred to add a predetermined amount of the alcohol to the synthetic liquid. In a method involving adding the synthetic liquid to the alcohol, the acid coexists in an excess amount of the alcohol, and therefore there is a possibility that water is produced. When water is produced in this system, the corrosiveness increases significantly to cause process hindrance, which is not preferred.

In this embodiment, the alcohol is not particularly limited, but lower alcohols having 1 to 3 carbon atoms, methanol, ethanol, n-propanol, and i-propanol, are preferred. Ethanol is preferred because the fragrance of TCDCE is excellent. One of these alcohols can be used alone, or two or more of these alcohols can be appropriately mixed and used.

The amount of the alcohol is not particularly limited but is preferably 1.0 to 1.5-fold moles based on DHDCPD. When the molar ratio of the alcohol is too low, there is a possibility that the esterification reaction does not proceed sufficiently, causing decrease in yield. Even if the alcohol is used in an amount higher than this range, the effects such as yield improvement are small, and there are possibilities that the cost of separating the alcohol increases, and that the volumetric efficiency of the apparatus also decreases.

The reaction temperature of the esterification is not particularly limited but is preferably 20° C. or less. When the reaction temperature is higher than 20° C., there is a possibility of causing the decomposition of the ester and the dehydration reaction of the added alcohol, and so on to increase the risk of producing water as a by-product in the system.

In this embodiment, the acid catalyst is distilled off from the obtained esterified product, and then purification is performed by an ordinary method such as distillation to obtain TCDCE.

EXAMPLES

This embodiment will be more specifically described below using Examples and Comparative Examples. This embodiment is not limited in any way by the following Examples.

Example 1

A stainless steel autoclave having an internal volume of 500 mL in which the internal temperature was controllable by a jacket was used, the stainless steel autoclave being equipped with a magnetic force induction type stirrer, three inlet nozzles in the upper portion, and one drawing nozzle at the bottom.

First, the atmosphere inside the autoclave was replaced by carbon monoxide, and then hydrogen fluoride was introduced in an amount of 8.0-fold moles based on DHDCPD (amount of hydrogen fluoride: 75.1 parts by mass). The temperature was set at 30° C., and the pressure was increased to 2 MPaG with carbon monoxide.

While the reaction temperature and the reaction pressure were maintained at 30° C. and 2 MPaG, respectively, 260.8 parts by mass of a dilute solution obtained by dissolving 63.0 parts by mass of DHDCPD in 157.4 parts by mass of the Endo form of TCD (constituent ratio of Endo form of TCD/Exo form of TCD: 100/0) as a TCD isomer mixture and 40.4 parts by mass of n-heptane (n-Hep) was supplied from the upper portion of the autoclave to synthesize acyl fluoride by carbonylation. After the completion of the supply of DHDCPD, stirring was continued for about 30 min until no absorption of carbon monoxide was observed.

Next, the reaction temperature was dropped to 5° C., and 26.0 parts by mass of ethanol (EtOH) (1.2-fold moles based on DHDCPD) was supplied from the upper portion of the autoclave at atmospheric pressure to perform esterification at 5° C. under atmospheric pressure under stirring for 30 min.

The reaction liquid was drawn in ice water from the bottom of the autoclave to separate the oil phase and the aqueous phase. Then, the oil phase was washed twice with 100 mL of a 2% caustic soda aqueous solution and twice with 100 mL of distilled water and dehydrated with 10 parts by mass of anhydrous sodium sulfate. The obtained liquid was analyzed by gas chromatography by an internal standard method. As a result, the yield of TCDCE was 77.9% (based on DHDCPD).

Example 2

TCDCE was obtained by the same method as Example 1, except that the amount of hydrogen fluoride was changed from 75.1 parts by mass to 81.9 parts by mass, the amount of DHDCPD was changed from 63.0 parts by mass to 68.7 parts by mass, the amount of the TCD isomer mixture was changed from 157.4 parts by mass to 103.0 parts by mass, the amount of n-heptane was changed from 40.4 parts by mass to 30.7 parts by mass (1.2-fold moles based on DHDCPD), and the amount of ethanol was changed from 26.0 parts by mass to 28.3 parts by mass.

The yield of TCDCE was 70.4% (based on DHDCPD).

Example 3

TCDCE was obtained by the same method as Example 1, except that the amount of hydrogen fluoride was changed from 75.1 parts by mass to 90.8 parts by mass, the amount of DHDCPD was changed from 63.0 parts by mass to 76.1 parts by mass, 114.2 parts by mass of a TCD isomer mixture having a constituent ratio, Endo form of TCD/Exo form of TCD, of 60/40 was used instead of 157.4 parts by mass of the TCD isomer mixture, the amount of n-heptane was changed from 40.4 parts by mass to 31.4 parts by mass, and the amount of ethanol was changed from 26.0 parts by mass to 28.3 parts by mass (1.1-fold moles based on DHDCPD).

The yield of TCDCE was 71.5% (based on DHDCPD).

Example 4

TCDCE was obtained by the same method as Example 1, except that the amount of hydrogen fluoride was changed from 75.1 parts by mass to 98.7 parts by mass, the amount of DHDCPD was changed from 63.0 parts by mass to 82.9 parts by mass, the amount of the TCD isomer mixture was changed from 157.4 parts by mass to 82.8 parts by mass, the amount of n-heptane was changed from 40.4 parts by mass to 30.6 parts by mass, and the amount of ethanol was changed from 26.0 parts by mass to 34.0 parts by mass (1.2-fold moles based on DHDCPD).

The yield of TCDCE was 68.0% (based on DHDCPD).

Example 5

TCDCE was obtained by the same method as Example 1, except that the amount of hydrogen fluoride was changed from 75.1 parts by mass to 93.3 parts by mass, the amount of DHDCPD was changed from 63.0 parts by mass to 62.6 parts by mass (the amount of hydrogen fluoride was changed from 8.0-fold moles to 10.0-fold moles based on DHDCPD), the amount of the TCD isomer mixture was changed from 157.4 parts by mass to 93.9 parts by mass, the amount of n-heptane was changed from 40.4 parts by mass to 28.0 parts by mass, and the amount of ethanol was changed from 26.0 parts by mass to 25.8 parts by mass (1.2-fold moles based on DHDCPD).

The yield of TCDCE was 72.3% (based on DHDCPD).

Comparative Example 1

TCDCE was obtained by the same method as Example 1, except that the amount of hydrogen fluoride was changed from 75.1 parts by mass to 83.0 parts by mass, the amount of DHDCPD was changed from 63.0 parts by mass to 69.6 parts by mass, 174.0 parts by mass of a TCD isomer mixture having a constituent ratio, Endo form of TCD/Exo form of TCD, of 50/50 was used instead of 157.4 parts by mass of the TCD isomer mixture, the amount of n-heptane was changed from 40.4 parts by mass to 30.1 parts by mass, and the amount of ethanol was changed from 26.0 parts by mass to 28.7 parts by mass (1.2-fold moles based on DHDCPD).

The yield of TCDCE was 67.0% (based on DHDCPD).

Comparative Example 2

TCDCE was obtained by the same method as Example 1, except that the amount of hydrogen fluoride was changed from 75.1 parts by mass to 108.4 parts by mass, the amount of DHDCPD was changed from 63.0 parts by mass to 90.9 parts by mass, 90.9 parts by mass of a TCD isomer mixture having a constituent ratio, Endo form of TCD/Exo form of TCD, of 50/50 was used instead of 157.4 parts by mass of the TCD isomer mixture, the amount of n-heptane was changed from 40.4 parts by mass to 32.6 parts by mass, and the amount of ethanol was changed from 26.0 parts by mass to 37.5 parts by mass (1.2-fold moles based on DHDCPD).

The yield of TCDCE was 66.0% (based on DHDCPD).

Comparative Example 3

TCDCE was obtained by the same method as Example 1, except that the amount of hydrogen fluoride was changed from 75.1 parts by mass to 83.3 parts by mass, the amount of DHDCPD was changed from 63.0 parts by mass to 69.8 parts by mass, 174.6 parts by mass of a TCD isomer mixture having a constituent ratio, Endo form of TCD/Exo form of TCD, of 0/100 was used instead of 157.4 parts by mass of the TCD isomer mixture, the amount of n-heptane was changed from 40.4 parts by mass to 43.6 parts by mass, and the amount of ethanol was changed from 26.0 parts by mass to 28.8 parts by mass (1.2-fold moles based on DHDCPD).

The yield of TCDCE was 59.6% (based on DHDCPD).

Comparative Example 4

TCDCE was obtained by the same method as Example 1, except that the amount of hydrogen fluoride was changed from 75.1 parts by mass to 103.2 parts by mass, the amount of DHDCPD was changed from 63.0 parts by mass to 86.5 parts by mass, 86.5 parts by mass of a TCD isomer mixture having a constituent ratio, Endo form of TCD/Exo form of TCD, of 0/100 was used instead of 157.4 parts by mass of the TCD isomer mixture, the amount of n-heptane was changed from 40.4 parts by mass to 27.9 parts by mass, and the amount of ethanol was changed from 26.0 parts by mass to 35.0 parts by mass (1.2-fold moles based on DHDCPD).

The yield of TCDCE was 57.2% (based on DHDCPD).

Comparative Example 5

TCDCE was obtained by the same method as Example 1, except that the amount of hydrogen fluoride was changed from 75.1 parts by mass to 113.1 parts by mass, the amount of DHDCPD was changed from 63.0 parts by mass to 94.8 parts by mass, the amount of the TCD isomer mixture was changed from 157.4 parts by mass to 47.4 parts by mass, the amount of n-heptane was changed from 40.4 parts by mass to 23.7 parts by mass, and the amount of ethanol was changed from 26.0 parts by mass to 39.0 parts by mass (1.2-fold moles based on DHDCPD).

The yield of TCDCE was 63.8% (based on DHDCPD).

Comparative Example 6

TCDCE was obtained by the same method as Example 1, except that the amount of hydrogen fluoride was changed from 75.1 parts by mass to 121.1 parts by mass, the amount of DHDCPD was changed from 63.0 parts by mass to 101.5 parts by mass, 52.2 parts by mass of a TCD isomer mixture having a constituent ratio, Endo form of TCD/Exo form of TCD, of 60/40 was used instead of 157.4 parts by mass of the TCD isomer mixture, the amount of n-heptane was changed from 40.4 parts by mass to 17.0 parts by mass, and the amount of ethanol was changed from 26.0 parts by mass to 41.9 parts by mass (1.2-fold moles based on DHDCPD).

The yield of TCDCE was 56.8% (based on DHDCPD).

Comparative Example 7

TCDCE was obtained by the same method as Example 1, except that the amount of hydrogen fluoride was changed from 75.1 parts by mass to 118.6 parts by mass, the amount of DHDCPD was changed from 63.0 parts by mass to 99.2 parts by mass, no TCD isomer mixture was used, the amount of n-heptane was changed from 40.4 parts by mass to 42.6 parts by mass, and the amount of ethanol was changed from 26.0 parts by mass to 41.0 parts by mass (1.2-fold moles based on DHDCPD).

The yield of TCDCE was 53.9% (based on DHDCPD).

Comparative Example 8

TCDCE was obtained by the same method as Example 1, except that the amount of hydrogen fluoride was changed from 75.1 parts by mass to 129.3 parts by mass, the amount of DHDCPD was changed from 63.0 parts by mass to 86.8 parts by mass, no TCD isomer mixture was used, the amount of n-heptane was changed from 40.4 parts by mass to 44.6 parts by mass, and the amount of ethanol was changed from 26.0 parts by mass to 35.8 parts by mass (1.2-fold moles based on DHDCPD).

The yield of TCDCE was 55.5% (based on DHDCPD).

The results of the Examples and the Comparative Examples are shown in Table 1.

TABLE 1

| | Examples | | | | | Comparative Examples | | | | | | | |
|---|---|---|---|---|---|---|---|---|---|---|---|---|---|
| | 1 | 2 | 3 | 4 | 5 | 1 | 2 | 3 | 4 | 5 | 6 | 7 | 8 |
| DHDCPD [parts by mass] | 63.0 | 68.7 | 76.1 | 82.9 | 62.6 | 69.6 | 90.9 | 69.8 | 86.5 | 94.8 | 101.5 | 99.2 | 86.8 |
| HF [parts by mass] | 75.1 | 81.9 | 90.8 | 98.7 | 93.3 | 83.0 | 108.4 | 83.3 | 103.2 | 113.1 | 121.1 | 118.6 | 129.3 |
| TCD isomer mixture [parts by mass] | 157.4 | 103.0 | 114.2 | 82.8 | 93.9 | 174.0 | 90.9 | 174.6 | 86.5 | 47.4 | 52.2 | 0 | 0 |
| n-Hep [parts by mass] | 40.4 | 30.7 | 31.4 | 30.6 | 28.0 | 30.1 | 32.6 | 43.6 | 27.9 | 23.7 | 17.0 | 42.6 | 44.6 |
| HF/DHDCPD [molar ratio] | 8.0 | 8.0 | 8.0 | 8.0 | 10.0 | 8.0 | 8.0 | 8.0 | 8.0 | 8.0 | 8.0 | 8.0 | 10.0 |
| TCD/DHDCPD [ratio by mass %] | 250 | 150 | 150 | 100 | 150 | 250 | 100 | 250 | 100 | 50 | 51 | 0 | 0 |
| Endo form of TCD/Exo form of TCD (constituent ratio) | 100/0 | 100/0 | 60/40 | 100/0 | 100/0 | 50/50 | 50/50 | 0/100 | 0/100 | 100/0 | 60/40 | — | — |
| CO pressure [MPaG] | 2.0 | ← | ← | ← | ← | ← | ← | ← | ← | ← | ← | ← | ← |
| Reaction temperature [° C.] | 30 | ← | ← | ← | ← | ← | ← | ← | ← | ← | ← | ← | ← |
| Aging time after raw material supply [min] | 30 | ← | ← | ← | ← | ← | ← | ← | ← | ← | ← | ← | ← |
| EtOH [parts by mass] | 26.0 | 28.3 | 28.3 | 34.0 | 25.8 | 28.7 | 37.5 | 28.8 | 35.0 | 39.0 | 41.9 | 41.0 | 35.8 |
| EtOH/DHDCPD [molar ratio] | 1.2 | 1.2 | 1.1 | 1.2 | 1.2 | 1.2 | 1.2 | 1.2 | 1.2 | 1.2 | 1.2 | 1.2 | 1.2 |
| Reaction temperature [° C.] | 5 | ← | ← | ← | ← | ← | ← | ← | ← | ← | ← | ← | ← |
| Aging time after ethanol supply [min] | 30 | ← | ← | ← | ← | ← | ← | ← | ← | ← | ← | ← | ← |
| TCDCE yield [mol %] | 77.9 | 70.4 | 71.5 | 68.0 | 72.3 | 67.0 | 66.0 | 59.6 | 57.2 | 63.8 | 56.8 | 53.9 | 55.5 |

As shown in Table 1, by adopting the production method of this embodiment, TCDCE can be efficiently obtained in high yield.

This application claims the benefit of Japanese Patent Application No. 2018-26132 filed on Feb. 16, 2018, the contents of which are incorporated herein by reference.

INDUSTRIAL APPLICABILITY

The production method of the present invention is industrially extremely useful because TCDCE useful as a perfume raw material can be obtained industrially simply, in high yield, and efficiently.

The invention claimed is:

1. A method for producing tricyclo[5.2.1.0$^{2,6}$]decane-2-carboxylate, the method comprising:
   reacting tricyclo[5.2.1.0$^{2,6}$]deca-3-ene in a dilute solution comprising the tricyclo[5.2.1.0$^{2,6}$]deca-3-ene with carbon monoxide in the presence of an acid catalyst, followed by reaction with an alcohol to produce tricyclo[5.2.1.0$^{2,6}$]decane-2-carboxylate, wherein
   the dilute solution comprises 100 parts by mass or more of a tricyclo[5.2.1.0$^{2,6}$]decane isomer mixture based on 100 parts by mass of the tricyclo[5.2.1.0$^{2,6}$]deca-3-ene,
   the tricyclo[5.2.1.0$^{2,6}$]decane isomer mixture comprises endo-tricyclo[5.2.1.0$^{2,6}$]decane and exo-tricyclo[5.2.1.0$^{2,6}$]decane, and
   a constituent ratio of endo-tricyclo[5.2.1.0$^{2,6}$]decane to exo-tricyclo[5.2.1.0$^{2,6}$]decane is greater than 1.0.

2. The method according to claim 1, wherein an amount of the acid catalyst used is from 4 to 25-fold moles based on the tricyclo[5.2.1.0$^{2,6}$]deca-3-ene.

3. The method according to claim 1, wherein in reacting the tricyclo[5.2.1.0$^{2,6}$]deca-3-ene in the dilute solution comprising the tricyclo[5.2.1.0$^{2,6}$]deca-3-ene with the carbon monoxide, a partial pressure of the carbon monoxide is from 0.5 to 5 MPaG.

4. The method according to claim 1, wherein the alcohol comprises ethanol.

5. The method according to claim 1, wherein the acid catalyst is a catalyst comprising hydrogen fluoride.

6. The method according to claim 1, wherein the constituent ratio of endo-tricyclo[5.2.1.0$^{2,6}$]decane to exo-tricyclo[5.2.1.0$^{2,6}$]decane is greater than 1.5.

7. The method according to claim 1, wherein the constituent ratio of endo-tricyclo[5.2.1.0$^{2,6}$]decane to exo-tricyclo[5.2.1.0$^{2,6}$]decane is 100:0.

* * * * *